United States Patent [19]

Kossovsky et al.

[11] Patent Number: 5,506,420
[45] Date of Patent: Apr. 9, 1996

[54] SEMICONDUCTOR BIO-ELECTRONIC DEVICES INCORPORATING BIOCHEMICAL STABILIZATION LAYERS

[75] Inventors: Nir Kossovsky; Andrew Gelman; H. James Hnatyszyn; Samir Rajguru, all of Los Angeles, Calif.

[73] Assignee: The Regents of the University of California, Oakland, Calif.

[21] Appl. No.: 306,004

[22] Filed: Sep. 14, 1994

[51] Int. Cl.$^6$ ................................................. H01L 35/24
[52] U.S. Cl. ............................................. 257/40; 257/642
[58] Field of Search ................................ 257/40, 52, 53, 257/442, 642, 643, 72

[56] References Cited

PUBLICATIONS

Bruening et al., "Polar Ligand Adsorption Controls Semiconductor Surface Potentials," *J. Am. Chem. Soc.* 1994, 116, 2972–2977, Mar. 1, 1994.
Retzinger et al., "The Role of Surface in the Biological Activities of Trehalose 6,6'-Dimycolate," *J. Biol. Chem.*, 1981, 256, 8208–8216, Aug. 1981.
Kleinfeld et al., "Stepwise Formation of Multilayered Nanostructual Films from Macromolecular Precursors," *Science* 1994, 265, 370–373, Jul. 1994.
Birge, R. R., "Protein–Based Three–Dimensional Memory," *Am. Sci.* 1994, 82, 348–355, Jul. 1994.
Kamenetsky et al., "Structure of Solidified Colloidal Array Laser Filters Studied by Cryogenic Transmission Electron Microscopy," *Science* 1994, 263, 207–210, Jan. 1994.
Yablonovitch, E., "The Chemistry of Solid–State Electronics," *Science* 1989, 246, 347–351, Oct. 1989.
Service, R. F., "Self–Assembly Comes Together," *Science* 1994, 265, 316–318, Jul. 1994.
Mahajan et al., "An Introduction to Semiconducting Materials and Related Technologies," *Concise Encyclopedia of Semiconducting Materials and Related Technologies*, 1992, xviii–xxiii, 51–66, 313–315, 363, 507 and 511.

Wu et al., "Conducting Polyaniline Filaments in a Mesoporous Channel Host," *Science* 1994, 264, 1757–1759, Jun. 1994.
Marguerettaz et al., "Heterodyads: Electron Transfer at a Semiconductor Electrode–Liquid Electrolyte Interface Modified by an Adsorbed Spacer–Acceptor Complex," *J. Am. Chem. Soc.*, 1994, 116, 2629–2630.
O'Regan et al., "A low–cost, high–efficiency solar cell based on dye–sensitized colloidal $TiO_2$ films," *Nature* 1991, 353, 737–740, Oct. 1991.
O'Regan et al., "Vectorial Electron Injection Into Transparent Semiconductor Membranes and Electric Field Effects on the Dynamics of Light–Induced Charge Separation," *J. Phys. Chem.*, 1990, 94, 8720–8726.
Colvin et al., "Semiconductor Nanocrystals Covalently Bound to Metal Surfaces with Self-Assembled Monolayers," *J. Am. Chem. Soc.*, 1992, 114, 5221–5230.
Yan et al., "Molecular Recognition through Intercalation Chemistry: Immobilization of Organoclays on Piezoelectric Devices," *J. Am. Chem.*, 1993, 5, 905–907.
Feng et al., "Growth of Oriented Molecular Sieve Crystals on Organophosphate Films," *Nature* 1994, 368, 834–836, Apr. 1994.
Flaxer et al., "Molecular Light Emission Induced by Inelastic Electron Tunneling," *Science* 1993, 262, 2012–2014, Dec. 1993.

(List continued on next page.)

*Primary Examiner*—Rolf Hille
*Assistant Examiner*—Minhloan Tran
*Attorney, Agent, or Firm*—Poms, Smith, Lande & Rose

[57] ABSTRACT

Improved bio-electronic devices in which a layer of a polyhydroxy oligomer is provided between the surface of a semiconductor material and an electronically active biochemical molecule which is designed to be bound to the semiconductor surface to provide an electronic device. The layer of polyhydroxy oligomer functions as a biochemical stabilization layer to prevent denaturization of the electronically active biochemical molecule.

10 Claims, 1 Drawing Sheet

OTHER PUBLICATIONS

Sucheta et al., "Reversible Electrochemistry of Fumarate Reductase Immobilized on an Electrode Surface. Direct Voltammetric Observations of Redox Centers and Their Participation in Rapid Catalytic Electron Transport," *Biochemistry*, 1993, 32, 5455–5465.

Schlautman et al., "Binding of a Fluorescent Hydrophobic Organic Probe by Dissolved Humic Substances and Organically–Coated Aluminum Oxide Surfaces," *Environ. Sci. Technol.*, 1993, 27, 2523–2532.

Gaines et al., "Photoinduced Electron Transfer in the Solid State: Rate vs Free Energy Dependence in Fixed–Distance Porphyrin–Acceptor Molecules," *J. Am. Chem. Soc.*, 1991, 113, 719–721.

May, M., "The Electric Eye," *Popular Science*, 1993, 60–62, 76.

Di Bella et al., "Environmental Effects on Nonlinear Optical Chromophore Performace. Calculation of Molecular Quadratic Hyperpolarizabilities in Solvating Media," *J. Am. Chem. Soc.*, 1994, 116, 4440–4445.

Bjørnholm et al., "Nonlinear Optical Phenomena due to Donor–Acceptor Interfaces Created in Langmuir–Blodgett Films," *J. Chem. Soc. Chem. Commun.*, 1992, 815–817.

Heinrich et al., "Luminescent Colloidal Silicon Suspensions from Porous Silicon," *Science*, 1992, 255, 66–68.

Seiler et al., "Photoinduced Electron Transfer in Supramolecular Assemblies Composed of Dialkoxybenzene–Tethered Ruthenium (II) Trisbipyridine and Bipyridinium Salts," *J. Am. Chem. Soc.*, 1994, 116, 3399–3404.

Kuroda et al., "Controlled Electron Transfer Between Cyclodextrin–Sandwiched Porphyrin and Quinones," *J. Am. Chem. Soc.*, 1993, 115, 7003–7004.

Lisensky et al., "Periodic Properties in a Family of Common Semiconductors," *J. Chem. Ed.*, 1992, 69, 151–156.

Flaxer et al., "Molecular Light Emission Induced by Inelastic Electron Tunneling," *Science*, 1993, 262, 2012–2014.

Yan et al., "Molecular Recognition on Acoustic Wave Devices: Sorption in Chemically Anchored Zeolite Monolayers," *J. Am. Chem. Soc.*, 1992, 96, 9387–9393.

SEMICONDUCTOR BIO-ELECTRONIC DEVICES INCORPORATING BIOCHEMICAL STABILIZATION LAYERS

BACKGROUND OF THE INVENTION

1. Field of the Invention

The present invention relates generally to bio-electronic devices in which one or more films of an electronically active biochemical material are placed on a semiconductor substrate. More particularly, the present invention relates to such bio-electronic devices where the electronic activity of the biochemical films or layers is preserved through the use of one or more biochemical stabilization layers which are located between the semiconductor and biochemical films and between the biochemical films themselves.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Semiconductors, materials that variably exhibit electrical conductivity, are used to fabricate solid-state electronic devices. Their utility arises from the property that their conductivity can change in response to environmental stimuli and because they are subject to photoelectric effects. Their properties arise from their crystalline nature, and become manifest at their surfaces.

Semiconductors are the product of a very creative and fortunate set of experiments performed in the 1940s by Shockley and Bardeen demonstrating the transistor effect (1). The consequences of their work has completely transformed the world over the latter half of the 20th century. Well recognized simple examples of semiconductor-based devices include the temperature-sensitive thermistor, makes use of the fact that semiconducting mixtures of certain metallic oxides decrease in electrical resistance with temperature increase. The device thus acts as a temperature sensor/switch, and enables a current to pass through that is proportional to the temperature change. Another semiconductor component is the light-sensitive photoconductive cell, or photoresistor. A photoresistor made from a thin film of cadmium sulfide has a resistance that can range from a high of millions of ohms in total darkness to a low of tens of ohms when it is illuminated with visible light. The device thus acts as a light sensor/switch and enables a current to pass through that is proportional to the, light change.

Diodes are devices that are based, in part, on the latter property of semiconductors, and those that have optoelectronic properties are especially important. Light-emitting diodes can be made from gallium arsenide, gallium phosphide, and certain other semiconductor compounds. These diodes emit a relatively narrow-frequency spectrum of optical radiation, which may range from the visible to the infrared, depending on the semiconductor from which the diode is made. Light-emitting diodes producing red, yellow, and green light have found widespread use as long-lived indicator lamps and as numeric displays in electronic calculators, wrist-watches, and other solid-state instruments. Infrared-emitting diodes are used for the optical transmission of information (optical communications) through highly transparent glass and plastic fibers, as well as through the atmosphere. The light-emitting diode laser is a junction diode that emits a narrow band of wavelengths of optical radiation when powered by an electric current above a specific threshold level.

Other kinds of optoelectronic diodes are used to detect optical radiation, some being specifically designed to detect various wavelengths and modulation frequencies. Solar cells are large-area junction diodes, most commonly made of doped silicon, that produce an electrical current in response to solar radiation having wavelengths ranging from the visible to the near infrared.

Other types of semiconductor devices include electronic switching devices such as silicon rectifiers, triacs and transistors.

The Materials Basis of Semiconductor Properties

One point that should be apparent from the above is that semiconductor materials are all essential crystalline ceramics. They may be metal oxide ceramics, intermetallic ceramics, or combinations thereof but tend to be comprised of elements in the central columns of the periodic table.

In chemical terms, what makes the semiconductor crystal so special is that the entire semiconductor crystal is a giant covalently bonded molecule. In semiconductors, electron wave functions are delocalized in principle over an entire macroscopic crystal. Because of the large spatial extent of these wave functions, no single atom can have much effect on the electron energies. Because semiconductors are drawn from the central columns (III, IV, V) of the periodic table and tend to be non-polar, electrons in both the valence and conduction bands (bonding and antibonding orbitals) tend to ignore the crystallographic lattice of atoms as well as one another. Therefore, instead of having one single chemical potential (or Fermi level) for all the electrons in the material, the possibility exists for two separate quasi-Fermi levels in the same crystal (2).

Semiconductor Surfaces are Critical to Their Function

Semiconductor surfaces are the most likely location for non-bonding or weakly bonding orbitals to occur. These non-bonding orbitals with unwanted energy levels in the forbidden gap may promote slow decay of electrons from the conduction band back into the valence band in a process that is known as "internal conversion". This is also known as non-radiative recombination. Defect levels, arising from impurities within the crystal mass (also known as dislocations), act as stepping stones permitting conduction of electrons to cascade down to the valence band (2). For this reason, semiconductor processing requires exquisite control of the materials' surfaces and the cleanliness controls for manufacturing exceed both aerospace and medical standards (3).

Advances in semiconducting materials and related technologies enabling improved solid state electronics have arisen from the ability to grow macroscopically dislocation-free large diameter silicon single crystals, controlled growth of thick epitaxial layers, advances in processing techniques and an understanding of the interrelationship between "microstructures and device behavior". The techniques used to grow crystals are the following: a) Czochralski, b) float zone, c) liquid encapsulated Czochralski, and d) Bridgman. Certain devices, such as light-emitting diodes, double heterostructures or lasers, quantum well lasers, photodetectors and solar cells, all require multi layer structures consisting of layers of different compositions and conductivity. Among the various techniques used to deposit epitaxial layers or otherwise modify the surfaces of semiconductors include: chemical vapor deposition, organo-metallic vapor phase epitaxy, molecular beam epitaxy, organo-metallic molecular beam epitaxy, diffusion techniques and ion implantation techniques (4).

One of the common features of almost all semiconductor devices is that they exhibit relatively linear responsivities (5). For example, thermistors produce a linearly proportional increase in conductivity relative to an environmental temperature increase, photoresistors produce a linearly proportional increase in conductivity relative to environmental visible light radiation increase, and diodes become linearly more luminescent with an increase in current.

While linear responsivity is extremely useful in a broad range of applications such as biotechnology, physics, chemistry, medicine, aviation, oceanography and environmental control (5), ultra sensitive detection systems in all of these fields of use would have to exhibit non-linear transduction—would have to produce a disproportionately large signal in response to an extremely low level of substance, and a disproportionately small signal in response to an extremely high level of substance—to be maximally useful.

In particular, low threshold detection has been a major technological challenge. The task is not physically impossible, for there are ample examples of naturally occurring ultra-sensitive detection systems with a broad dynamic range. Indeed, biological systems are optimized for low level detection. Animals have optical and acoustic detection systems that are far more sensitive and have a far greater dynamic range than any manmade device. Insects and fish have extraordinary chemoreceptors far more sensitive than any synthetic device. Mimicry of these biological non-linear systems in a synthetic device, however, has only recently been explored.

Recent studies have shown that modifications in the surfaces of semiconductors can have a profound impact on their electrical performance. This is particularly true for polycrystalline semiconductor devices such as CdTe- and CuInSe$_2$ based solar cells (7). Specifically, several recent studies have shown that exposure of semiconductors to organic ligands can change both semiconductor luminescence or flat band potentials (8, 9). In the primary study cited, semiconductor's electron affinity (surface conductivity) was modifiable over a 500 mV range with various substituted benzoic acid derivatives without affecting band bending. These findings suggest that semiconductors may function as chemoreceptors/sensors in a manner analogous to thermistors and photoresistors.

Organized Complex Molecules (Homodyads)

The rediscovery of surfaces has led to investigations in two directions. The first involves exploration of devices based exclusively on surface elements while the other involves exploration of bulk device tuning through surface modification. As an example of the former, efforts to create electronic functions and devices based on molecules instead of bulk semiconductors are being inspired by the anticipated enormous increase in computing speed and storage density. Among the challenges of coupling conjugated systems and confined aromatic systems with operational devices is to achieve charge transfer in low fields such as metallic wires and to establish communication with individual electrically separated nanometer structures or molecules. Conjugated polymers with mobile charge carriers in nanometer channels that exhibit significant conductivity when encapsulated have been described. The materials used include the mesoporous alumino-silicate host, designated MCM-41 and the conducting polymer, polyaniline (10). Organized complex molecules, known also as homodyads or dyads, have been fabricated from a wide variety of materials. Homodyads are simply paired electron donor molecules and electron acceptor molecules separated by a spacer molecule (11).

Organized Complex Electronically Active Molecules at Semiconductor Surfaces (Heterodyads)

Both the surface modification concept and the electron donor-acceptor pair concept can be combined at the semiconductor surface. Electron transfer across the space between a donor semiconductor and an acceptor organic molecule has been demonstrated in a three layered construct comprised of polycrystalline titanium dioxide, a salicylic acid related spacer molecule, and an electron acceptor from the bipyridinium family (12). The product was viewed as a regenerative photoelectrical cell based on transparent polycrystalline semiconductor films sensitized by chemisorbed dyes (13, 14). Many others have been involved in similar types of experiments.

Colvin et al. (15) describe a method for attaching semiconductor nanocrystals to metal surfaces using self assembled difunctional organic monolayers as bridge compounds. Recent advances have extended self assembled monolayers beyond the prototype gold/thiol systems. Fatty acids on aluminum, silanes on silicon, isonitriles on platinum and rigid phosphates on metals are all examples. Metals provide the ideal support for organic compounds with large non-linear optical behavior and by using self assembled monolayers, the molecules can be held in specific orientations with respect to the metal (16). In other work, the ability to dictate the structural details of an interface is exploited to study processes of electron transport between an electrode surface and an active moiety bound on top of a monolayer (17, 18, 19).

Yan and Bein demonstrate the potential of organically modified layered sorbents for the development of selective chemical sensors, for example, for aromatic compounds. The interplay of size exclusion and partitioning in the organic phases results in unique selectivities that can complement the molecular sieving of porous framework hosts such as zeolites. Shown is a four layer composition comprised of a silicate layer, an organic clay layer which is the molecular sieve and binding layer, an additional silicate and finally, a QCM gold electrode sensor (20).

Feng and Bein (12) reported the oriented growth of crystals of zinc-phosphate zeolite in gold surfaces modified with metal phosphonate multilayer films. The high degree of orientation observed is attributed to a strong affinity between the phosphonic acid groups of the phosphate multi layer and the (111) faces of the growing crystals. The systems described are the first examples of oriented surface controlled growth of molecular sieve crystals. These materials, they suggested could offer exciting applications such as controlled access of molecules of pre-selected size to a sensor surface or orientation of moleculars for non-linear optical applications.

In general, the very low light emission efficiency from the molecules adjacent to metallic and semiconductor surfaces is caused by the fast deexcitation processes governed by energy transfer to non-radiative surface excitations (Auger processes). Conductors such as indium-tin-oxides, which possess band structures that are responsible for the optical transparency in the visible and near ultraviolet and therefore preclude efficient energy transfer in this energy range become an ideal surface to measure light emission from immobilized molecules on their surfaces. Indium-tin-oxide surfaces were coated with high emission and photochemically stable molecules 9–10 dichloro\anthracene and the laser dyes DCM and coumarin (21).

The design of selective coatings for microsensors such as optical waveguides, chemically sensitive field effect transistors, chemical resistors and acoustic wave devices has attracted growing attention. The goal of these studies is to increase the sensitivity and chemical selectivity of the sensor by controlling the surface interactions and solubilities of analyte vapors to be detected. Yan and Bein (22) use the coupling agent 3-mercaptopropyl-trimethoxysilane as a bifunctional molecular precursor for anchoring zeolite crystals to a gold electrode. A three layer composition comprised of a gold tin oxide quartz crystal microbalance coated with a cat ionic disilane coated with a zeolite arrangement has been used to control the self assembly of redox chains on electrodes (23).

Part of the problem of introducing non-linear functionality to semiconductor devices, essentially coupling allosteric electronically active biological molecules to the surfaces of semiconductors, arises from the molecular inactivation induced by the surfaces. It is important to note that not all molecules that are electron-active lose their activity following surface mobilization. Fumarate reductase from *E. coli* can be immobilized in an extremely electroactive state at an electrode with a retention of native catalytic properties. Fumarate serves as a terminal electron acceptor (24). In addition, many of the molecules which form homodyads may retain activity after being surface bound, although there is little data at present to support such a contention. More importantly, surface induced denaturation is well recognized. Loss of fluorescence activity after direct adsorption to solid surfaces, such as glass observed by Schlautman (25) using the dye perylene. The fluorescence of polycyclic aromatic hydrocarbons tends to be observed only with free solute and almost universally is quenched following adsorption or other association of non-organic materials. Fluorescence quenching of perylene approached almost 100% with the binding of perylene to humic acid as well, while bovine serum albumin quenched only 42% of the associated perylene fluorescence (25). In a similar vein, Gaines et al. have shown that a dyad may be stabilized by as much as 0.9 eV in going from a polar liquid to a rigid glass (26). Thus, solid states are clearly, in general, inhibitory of optimal electron carriage by electronically active biological molecules.

Surfaces also tend to constrain a molecule's ability to assume various allosteric conformations. This can negatively impact the performance of certain bio-opto/electronic devices. For example, optical memory devices, by virtue of the band width of laser devices, are expected to improve the density of microprocessor memory by a factor of 10. During the past eight years, investigators have shown considerable interest in using light-transducing proteins for optical memories. The use of biological molecules has significant advantages. The ability of biological molecules to respond to photons and convert to electrical energy in part, depends on changes in molecular shape. The shape change induces changes in a molecule's frequency response which could make a device based on shape-changing molecules self tuning as well as nonlinear (27). Restricting the allosteric activity by a non-yielding surface would preclude the realization of the projected gain.

Biosensors are another class of devices dependent on shape. Biosensors are analytical devices that respond selectively to analytes in an appropriate sample and convert their concentration into an electrical signal via a combination of a biological recognition system and a physico-chemical transducer. Biosensors promise to provide a powerful and inexpensive alternative to conventional analytic strategies for assaying chemical species in complex matrices; they do this by being able to discriminate the target analyte from a host of inert and potentially interfering species without the requirement for separating and, subsequently, identifying all the constituents of the sample. Specific fields of applications include veterinary medicine, agri-food, horticulture, pharmaceutics, petrochemical industry, environmental surveillance, defense and security (28). All biosensors exploit a close harmony between a selective biorecognition system and a transducer which translates a physico-chemical signal perturbation associated with the biorecognition process into a usable signal. The biorecognition system is typically an enzyme, sequence of enzymes, lectin, antibody, membrane receptor protein, organelle, bacterial, plant or animal cell or whole slice of plant or mammalian tissue. The majority of successful biosensors exploit enzymes as a biological recognition response system which are linked to transducers capable of responding to the protons, ions, gasses, heat, light, mass or electrons generated during the catalytic cycle. Biocatalytic systems based on enzymes can display poor stability, limited selectivity and insufficient sensitivity at low levels. Highly selective and sensitive devices based on immunological recognition systems may circumvent the shortcomings. One example of an antibody system included a surface acoustic wave quartz crystal which was comprised of interdigitated transducers between which was deposited a goat antibody by covalent immobilization to the silanized surface (29).

In general, the coupling of the semiconductor materials to biologically active molecules or even living tissues is extremely difficult, and the contact must be "gentle" (30). More technically, optimization of molecular response of nonlinear optical materials will depend crucially on how the chromophore molecule response is affected by environment and the temporal characteristics of that environment (31).

SUMMARY OF THE INVENTION

In accordance with the present invention, improved bio-electronic devices are provided wherein the electronic activity of biochemical molecules is preserved when they are located on the surface of a semiconductor electronic device. The present invention is based on the discovery that a layer of polyhydroxy oligomer placed between the semiconductor surface and the layer of electronically active biochemical molecules prevents or substantially reduces any denaturization of the biochemical molecule or other lessening of electronic activity.

Bio-electronic devices in accordance with the present invention include an electronic device which includes at least one semiconductor layer having a surface formed from semiconductor layer material. A biochemical stabilization layer is deposited on and bound to the semiconductor surface. The biochemical stabilization layer is made up of a polyhydroxy oligomer. The stabilization layer has an interior surface in contact with and bound to the semiconductor layer surface. Further, the stabilization layer of polyhydroxy oligomer has an exterior surface. To this exterior surface is bound the electronically active biochemical molecule which functions in conjunction with the underlying electronic device to provide a bio-electronic device. The present invention may be used to prevent or substantially reduce deactivation of electronically active biochemical molecules when they are bound to semiconductor material surfaces present in an electronic device.

The above discussed and many other features and attendant advantages of the present invention will become better understood by reference to the following detailed description of the invention.

DETAILED DESCRIPTION OF THE INVENTION

The present invention is directed to bio-electronic devices in which electronically active biochemical materials are used in combination with a semiconductor material. In such devices, the biochemical material is deposited or otherwise applied to the surface of the semiconductor substrate to form a layer of biochemical material which electronically interacts with the semiconductor substrate. In accordance with the present invention, any denaturization of the biochemical material which might be caused by the semiconductor material is eliminated or substantially reduced by placing a stabilization layer of polyhydroxy oligomers between the biochemical material and the semiconductor.

Figure 1:
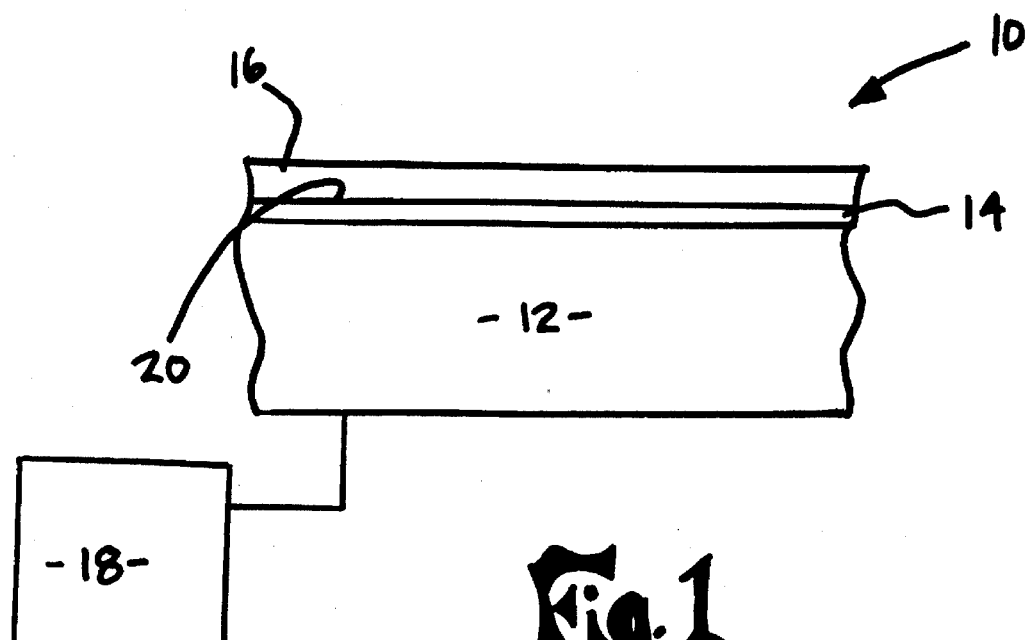
FIG. 1 is a schematic representation of an exemplary bio-electronic device in accordance with the present invention wherein a layer of electronically active biochemical material is bound to the surface of a semiconductor substrate via a stabilization layer of polyhydroxy oligomer.

A simplified schematic representation of a preferred exemplary bio-opto-electronic device in accordance with the present invention is shown generally at 10 in FIG. 1. The device 10 includes a semiconductor substrate 12, a stabilization layer 14 and a layer 16 of electronically active biochemical material. The semiconductor substrate 12 is connected to other conventional electronic elements, as represented by box 18, which are required to provide a fully functioning bio-electronic device. These electronic elements 18 are standard electronic parts which are known to those skilled in the art and will not be described in detail.

The electronically active biochemical material used to form layer 16 may be any of the known biochemical materials which are used in conjunction with semiconductors in bio-electronic devices and especially bio-opto-electronic devices. Exemplary biochemical materials include rhodopsin, fluorescein, chlorophyll, cytochrome C, oxido reductase with phospholipid, photosystem I protein, photosystem II protein, quinones, such as hydroquinone, ubiquinone, NAD reductase and electron donor and electron acceptor molecules such as those listed in Tables 1 and 2 below.

TABLE 1

| Electron Donors (D) | Electron Acceptors (A) |
|---|---|
| Octadecylthio-1 | 4,4' bipyridinium perchlorate |
| bacteriorhodopsin | bipyridinium salts: |
| ruthenium (II) tris{4,4'- | N,N'-dimethyl-4,4' |
| bis[(methyl- | bipyridinium |
| eneoxy)tris(ethyleneoxy)(4- | $MV^{2+}$ |
| methoxybenzene)]-2,2'- | cyclo[bis(N,N'-p-xylylene- |
| bipyridine} | 4,4'-biyridinium)] |
| para-xylene | $BXV^{4+}$ |
| 1,2,4-trimethylbenzene | 2,6,9,10-tetracyanoanthracene |
| durene | octadecylthiobenzoquinone |
| pentamethylbenzene | 9-10 dichloro-anthracene |
| hexamethylbenzene | DCM |
| {7-(N- | coumarin |
| octaadodecylaminomethyl)-8- | |
| 16-dioxadenzo[f,g]perylene} | |

TABLE 2

Donor-Acceptor II Conjugated Chromophores

1. D = $N(CH_3)_2$, A = $NO_2$, n = 1
2. D = $OCH_3$, A = $NO_2$, n = 1
3. D = $N(CH_3)_2$, A = $NO_2$, n = 2
4. D = $OCH_3$, A = $NO_2$, n = 2
5. D = $N(CH_3)_2$, A = $NO_2$, n = 3
6. D = $OCH_3$, A = $NO_2$, n = 3
7. D = $N(CH_3)_2$, A = $NO_2$, n = 4
8. D = $OCH_3$, A = $NO_2$, n = 4
9. D = $OCH_3$, A = COH, n = 1
10. D = $OCH_3$, A = COH, n = 2
11. D = $OCH_3$, A = COH, n = 3
12. D = $N(CH_3)_2$, A = $NO_2$, n = 1

The semiconductor materials used to form the semiconductor substrate 12 can also be any of the conventional materials typically used to form semiconductors for use in electronic devices. Exemplary semiconductor materials include photovoltaic materials such as those set forth in Table 3.

TABLE 3

SEMICONDUCTOR MATERIALS

| Material | Efficiency (%) |
|---|---|
| Semicrystalline (polycrystalline wafer) homojunctions | |
| silicon | 14 |
| Schottky, MIS, SIS | |
| indium tin oxide-silicon (SIS) | 8.5 |
| tin oxide-silicon (SIS) | 10 |
| silicon (MIS) | 8.8 |
| Polycrystalline (thin films) homojunctions | |
| silicon ($n^+p$ SOC, Si—MG—Si-graphite) | 9–10 |
| GaAs ($n^+p$) | 6.5 |
| heterojunctions | |
| $Cu_2S$—CdS | 9–10 |
| $Cu_2S$—CdZnS | 9 |
| $CuInSe_2$—CdS | 6 |
| InP—CdS | 3 |
| $Cu_2Te$—CdS | 6 |
| Schottky, MIS, SIS | |
| GaAs (MIS) | 6 |
| Amorphous (thin films) Schottky, MIS, SIS | |
| silicon (Schottky) | 6 |
| silicon (MIS) | 4.8 |
| homojunctions | |
| silicon ($n^+p - n^+/n/p/p^+$) | 13–20 |
| gallium arsenide | 22 |
| indium phosphide | 6 |
| GaAlAs-gallium arsenide | 18 |
| heterojunctions | |
| pCu2S-nSi | 5 |
| pInP-nCdS | 14 |
| pCdTe-nCdS | 8 |
| Schottky, MIS, SIS | |
| silicon (MIS) | 12 |
| gallium arsenide (MIS) | 15 |
| indium tin oxide-silicon (SIS) | 13 |
| tin oxide-silicon (SIS) | 12 |

Other exemplary semiconductor materials which may be used to form the semiconductor include C, Si, Ge, α-Sn, SiC, BN, BP, BAs, AlN, AlP, AlAS, AlSb, GaN, GaP, GaAs, GaSb, InN, InP, InAs, InSb, BeO, BeS, SeSe, BeTe, MgTe, ZnO, ZnS, ZnSe, ZnTe, CdS, CdSe, CdTe, HgS, HgSe, HgTe, CuF, CuCl, CuBr, CuI, AgI, Si-Ge, AlAs-Ge, AlAs-GaAs, $Al_xGa_{1-x}AsGaAs$ (Average value: x=0.09–0.7), $Al_xIn_{1-x}As$-InP (x=0.48, staggered gaps), AlSb-GaSb, GaAs-Si, GaAs-Ge, GaAs-InAs, GaP-Ge, GaP-Si, GaSb-Ge, GaSb-Si, InAs-Ge, InAs-Si, $InP-In_xGa_{1-x}As$ (x=0.53), $In_xAl_{1-x}AsIn_yGa_{1-y}As$ (x=0.52, y=0.53), InP-(In,Ga),(As, P), InP-Ge, InP-Si, $In_xGa_{1-x}P$-GaAs, InSb-Ge.

The stabilization layer 14 is made up of one or more polyhydroxy oligomers which provide an outer layer on the semiconductor to which the electronically active biochemical molecules may be bound without undergoing the denaturization associated with direct binding of the biochemical molecules to the surface of the semiconductor. Exemplary polyhydroxy oligomers which may be used to form the stabilization layer include carbohydrates, carbohydrate derivatives, and other macromolecules with carbohydrate-like components characterized by the abundance of —OH (hydroxyl) side groups. The coatings may include, but are not limited to:

- short chain carbohydrates including glucose, sucrose, cellobiose, nystose, triose, dextrose, trehalose, glucose, lactose and maltose.
- hydroxyl rich weak acids such as citrate, fumarate, succinate, isocitrate, oxaloacetate and realate.
- nucleotide-like molecules with pendant carbohydrate or phosphate groups such as pyridoxyl-t-pyrophosphate, thiamine pyrophosphate, uridine-diphosphate-glucose, glucose-1-phosphate, adenosine, nicotinamide-adenine-diphosphate, etc.
- derivatives of carbohydrates such as nitrocellulose.
- complex polymeric carbohydrates and derivatives such as dextran, glycogen, cellulose and chitin. Preferred polyhydroxy oligomers include cellobiose, pyridoxyl-5-pyrophosphate and citrate.

The polyhydroxy oligomers may be applied to the semiconductor surface in a variety of different ways to form the stabilization layer. Exemplary procedures involve pouring or spraying the polyhydroxyoligomer onto the semiconductor surface or dipping the semiconductor in a solution of the polyhydroxy oligomer. It is important that the surface of the semiconductor be ultraclean to insure formation of the desired stabilization layer. Any of the well-known procedures for producing ultraclean semiconductor surfaces may be used. For example, the cleaning procedure using hot methanol in combination with alumina polish and sonication as described by Bruenig (7) may be used. Other suitable cleaning techniques include plasm glow discharge and/or cleaning with NaCl and sodium bicarbonate followed by thorough rinsing with double distilled HPLC grade water.

In a preferred process, the ultraclean surface of the semiconductor is exposed to an ultrapure aqueous solution of the polyhydroxy oligomer by dipping the semiconductor in the solution or simply applying the solution to the semiconductor surface. The semiconductor is left in contact with the solution for a sufficient time to form a stabilization layer having the desired thickness.

The polyhydroxy oligomer solution into which the semiconductor is placed may contain from 1 to 30 weight/volume percent of the polyhydroxy oligomer. The solute is preferably double distilled water (ddH$_2$O). The semiconductor surface is maintained in the coating solution for a sufficient time to provide uniform coating of the surface. Emersion times ranging from 30 minutes to a few hours at room temperature are usually sufficient to form a suitable stabilization layer. The thickness of the stabilization layer is preferably from 1 nanometer to 100 nanometers.

Once the stabilization layer 14 has been formed, the electronically active biochemical material is coated onto the exterior surface 20 of the stabilization layer 14 to form layer 16. The particular procedure used to form the layer of electronically active biochemical material 16 will vary depending upon the particular material being deposited. Solution deposition as well as vapor phase deposition processes may be used. The thickness of layer 16 will also vary depending upon the particular biochemical material being used and the particular electronic device being made. For most bio-electronic devices, the biochemical material layer will have thicknesses ranging from 1 nanometer to about 100 nanometers.

Figure 2:
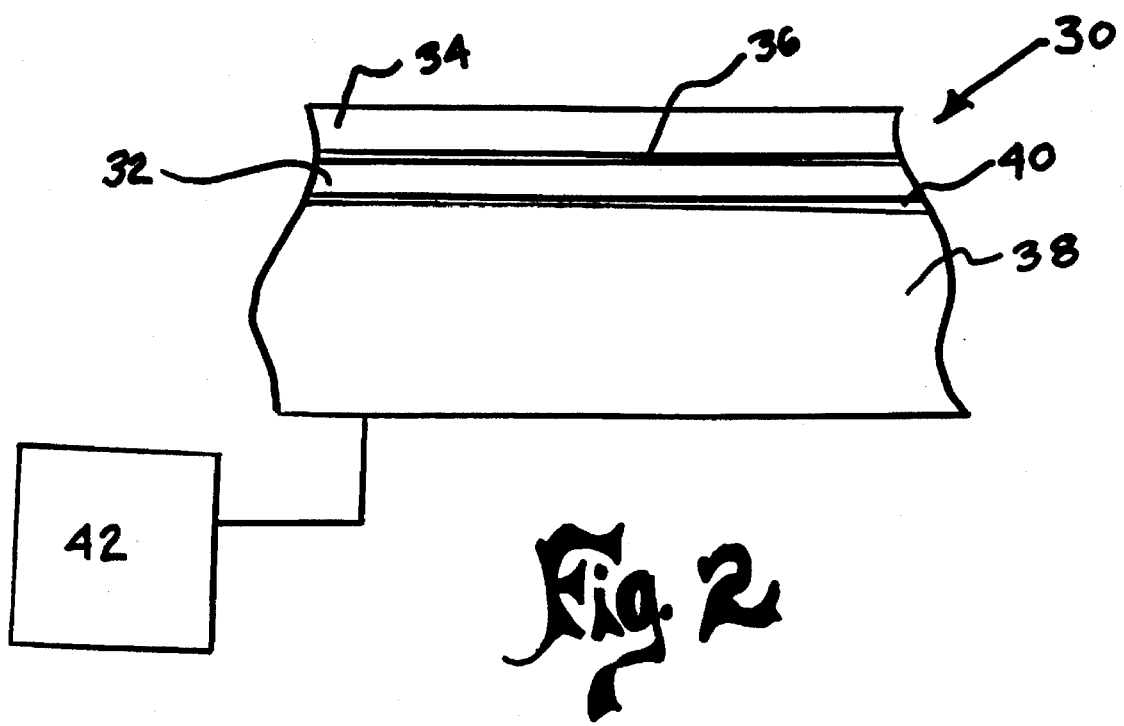
FIG. 2 is a schematic representation of an exemplary bio-electronic device in accordance with the present invention wherein two layers of electronically active biochemical material are bound to the surface of a semiconductor substrate wherein stabilization layers of polyhydroxy oligomers are placed between the semiconductor substrate and the stabilization layers and between the stabilization layers themselves.

A second exemplary bio-electronic device in accordance with the present invention, is shown generally at 30 in FIG. 2. The device 30 is similar to the device 10 shown in FIG. 1 except that it includes two layers of electronically active biochemical material 32 and 34. The two layers of biochemical material are made from the same type of materials used to form the electronically active biochemical material layer 16 present in device 10. The two layers 32 and 34 are separated by a stabilization layer 36 which prevents or substantially reduces any denaturization of the biochemical materials which might result from incompatibility between the materials. The interior electronically active biochemical layer 32 is separated from the semiconductor 38 by a stabilization layer 40. The semiconductor 38 is in turn connected to other electronic elements represented by box 42 to provide desired electronic devices.

The two electronically active biochemical material layers 32 and 34 may be deposited onto the surface of the semiconductor in the same manner as described above for device 10 provided that the stabilization layers 36 and 40 are deposited between the two layers themselves and between the layers and the semiconductor surface. The present invention is not limited to devices having one or two electronically active biochemical layers. Bio-electronic devices having as many layers as desired may be made in accordance with the present invention provided that each of the biochemical layers is separated from the others by a stabilization layer of polyhydroxy oligomers.

Examples of combinations of semiconductor substrate, stabilization layers and electronically active biochemical layers which can be used in bio-electronic and bio-optoelectronic devices is as follows:

| Semiconductor | Stabilizer | Biochemical Layers |
|---|---|---|
| silicon tin oxide | cellobiose | rhodopsin |
| silicon tin oxide | cellobiose | rhodopsin/fluorescein |
| gallium arsenide | cellobiose | rhodopsin/fluorescein |
| silicon tin oxide | cellobiose | cytochrome-C/ rhodopsin |
| cadmium sulfide | cellobiose | photosystem I protein/photosystem II protein |
| gallium arsenide | trehalose | photosystem I protein/photosystem II protein |
| cadmium telluride | maltose | rhodopsin |
| indium phosphide | zylotol | cytochrome-C/oxido reductase with phospholipid |

Examples of practice are as follows:

Preparation of Aqueous Solutions of Polydroxy Oligomers

Solutions of mono-, oligo- and polysaccharides were prepared as follows: 200 mM sorbitol and xylitol (Sigma, St Louis, Mo.; D-sorbitol, $C_6H_{14}O_6$ and xylitol, $C_5H_{12}O_5$, FW=182.2 and 152.1, respectively, solid-form) and 100 mM maltose, trehalose, sucrose, (Sigma, St Louis, Mo.; maltose $C_{12}H_{22}O_{11} \cdot H_2O$, FW=360.3; D-(+)trehalose $C_{12}H_{22}O_{11} \cdot 2H_2O$, FW =378.3; sucrose $C_{12}H_{22}O_{11}$ FW=342.3; solid form) and lactitol (Xyrofin Oy's, Kotka, Finland; lactitol $C_{12}H_{24}O_{11} \cdot H_2O$, FW=362.4, solid-form) were dissolved in HPLC-grade water. Two percent viscosity α-methyl cellulose (Sigma, St Louis, Mo.; α-methyl cellulose, 4000 centipoise, solid form) was dissolved in HPLC-grade water. All solutions are used within 14 days of preparation and stored at 4° C. between experiments.

Preparation Of Semiconductor Surface

Horizontal ZnSe-45° ATR specimen holder (Spectra-Tech model, Stamford, Conn.) plates were thoroughly washed with a solution of 100 mM NaCl and 100 mM $NaHCO_3$, followed by HPLC-grade water and acetone. Films of various polyhydroxyoligomers were then adsorbed onto the clean surface of the semiconductor by evenly applying 400 ul of the respective polyhydroxyoligomer solutions and lyophilizing for ten minutes without applied heat or rotation (Savant SVC 190 lyophilizer, Wesbury, N.Y.).

Addition of Electronically Active Biochemical Layers

Rhodopsin and fluorescein were deposited onto the various semiconductor surfaces using the Langmuir-Blodgett film technique. Layers of the donor (or acceptor) molecule, or multiple layers in a complex multilayered device with insulation layers added, were transferred to the coated semiconductor surfaces using a double LB trough (KSV Instruments, Finland, Model 5000-3). The downstroke occurred through the donor layer and the upstroke through an acceptor (or insulator) layer. The entire process was conducted in the darkness in order to prevent photoinduced endoperoxide formation from the donor. All of the above deposited biochemical films were found to retain their electronic activity after deposition onto the semiconductor surface.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

BIBILIOGRAPHY

1. Shockley, W., *Electrons and holes in semiconductors*, van Nostrand Rhineholt, New York, 1950.
2. Yablonovitch, E., The chemistry of solid-state electronics, *Science* 246:347–351, 20 Oct. 1989.
3. Service, R. F., Self-assembly comes together, *Science* 265:316–318, 15 Jul. 1994.
4. Mahajan, S., Kimerling, L. C., An introduction to semiconducting materials and related technologies, Concise Encycl. of Semiconducting Mat. & Rel Technol., 1992.
5. Irvine, C. E., The New Grolier Electronic Encyclopedia (TM) (c) 1991 Grolier Electronic Publishing, Inc.
6. Sadana, A. and Ram, A. B., Fractal analysis of antigen-antibody binding kinetics: Biosensor applications, *Biotechnology Progress*, 1994, 10, 291–298.
7. Bruening, M., Moons, E., Yaron-Marcovich, D., Cahen, D., Libman, J. and Shanzer, A., Polar ligand adsorption controls semiconductor surface potentials, *J. Am. Chem. Soc.* 1994, 116, 2972–2977.
8. Neu, D. R., Olson, J. A., Ellis, A. B., *J Phys. Chem.*, 97:5713–5716, 1993.
9. Hickman, J. J., Wrighton, M. S., *J. Am. Chem. Soc.*, 113:4440–4448, 1991.
10. Wu, C-G, and Bein, T., Conducting polyaniline filaments in a mesoporous channel host, *Science* 264:1757–1759, 17 Jun. 1994.
11. Marguerettaz, Z., O'Neill R., Fitzmaurice, D., Heterodyads: electron transfer at a semiconductor electrode-liquid electrolyte interface modified by an adsorbed spacer-acceptor complex, *J. Am. Chem. Soc.*, 116:2629–2630, 1994.
12. Feng, S. and Bein, T., *Nature*, 368:834–836, 28 Apr 1994.
13. O'Regan, B., Graetzel, M., *Nature*, 353:737, 1991.
14. O'Regan, B., Moser, J., Anderson, M., Graetzel, M., *J. Phys. Chem.*, 94:8270, 1990.
15. Colvin, V. L., Goldstein, A. N., Alivisatos, A. P., Semiconductor nanocrystals covalently bound to metal surfaces with self-assembled monolayers, *J. Am. Chem. Soc.*, 114, 5221–5230, 1992.
16. Putvinski, T. M., Schilling, M. L., Katz, H. E., Chidsey, C. E. D., Mujsce, A. M., Emerson, A. B., *Langmuir*, 6, 1567–1571, 1990.
17. Chidsey, C. E. D., *Science*, 251,919–922, 1991.
18. Chidsey, C. E. D., Bertozzi, C. R., Putvinski, T. M., Mujsce, A. M., *J. Am. Chem. Soc.*, 112: 4301–4306, 1990.
19. Chidsey, C. E. D., Loiacono, D. N., *Langmuir*, 6: 682–691, 1990.
20. Yan, Y., Bein, T., Molecular recognition through intercalation chemistry: iramobilization of organoclays on piezoelectric devices, *Chem of Materials*, 5: 905–907, 1993.
21. Flaxer, E., Sneh, O., Cheshnovsky, O., Molecular light emission induced by inelastic electron tunneling, *Science*, 262:2012–2014, 24 Dec. 1993.
22. Yan, Y., Bein, T., Molecular recognition an acoustic wave devices: sorption in chemically anchored zeolite monolayers, *J. of Phys. Chem*, 96 (23):9387–9393, 1992.
23. Li, Z., Lai, C., Mallouk, T. E., *Inorg. Chem*, 28:178, 1989.
24. Meyer, G. J., Leung, L. K., Yu, J. C., Lisensky, G. C., Ellis, A. B., *J. Am. Chem. Soc.*, 111:5146–5148, 1989. Sucheta, A., Cammack, R., Weiner, J., Armstrong, F. A., Reversible electrochemistry of fumarate reductase immobilized on an electrode surface. Direct voltammetric observations of redox centers and their participation in rapid catalytic electron transport, *Biochemistry*, 32 (20):5455–5465, 1993.
25. Schlautman, M. A., Morgan, J. J., Binding of a fluorescent hydrophobic organic probe by dissolved humic substances and organically-coated aluminum oxide surfaces, *Environ. Sci. Technol.* 27 (12):2523–2532, 1993.
26. Gaines, G. L., O'Neil, M., Svec, W. A., Niemczyk, M. P., Wasielewski, M. R., *J. Am. Chem. Soc.* 113:719–721, 1991.
27. Birge, R. R., Protein-based three-dimensional memory, *American Scientist*, 82:348–355, July –August 1994.
28. Higgins, I. J., Lowe, C. R., *Philos Trans R Soc London*, B324:487–496, 1989.
29. Lowe, C. R., Yon Hin, B. F. Y., Cullen, D. C., Evans, S. E., Stephens, L. D. G., Maynard, P., *J. of Chromatography*, 510:347–354, 1990.
30. May, M., The electric eye, *Popular Science*, 60–62, 76, August 1993.
31. Di Bella, S., Marks, T. J., Ratner, M. A., Environmental effects on nonlinear optical chromophore performance. Calculation of molecular quadratic hyperpolarizabilities in solvating media, *J. Am. Chem. Soc.*, 116: 4440–4445, 1994.

What is claimed is:

1. A bio-electronic device comprising:

a semiconductor layer having a surface consisting essentially of a semiconductor material;

a biochemical stabilization layer consisting essentially of a polyhydroxy oligomer, said stabilization layer having a) an interior surface in contact with and bound to said semiconductor layer surface and b) an exterior surface;

a layer of electronically active biochemical molecules bound to said exterior surface of said biochemical stabilization layer to provide an electronically active biochemical layer having its own exterior surface.

2. A bio-electronic device according to claim 1 wherein said semiconductor material is selected from the group consisting of silicon, indium tin oxide, tin dioxide and silicon tin oxide.

3. A bio-electronic device according to claim 1 wherein said semiconductor material is an amorphous material selected from the group consisting of gallium arsenide, indium phosphide, cadmium telluride and cadmium sulfide.

4. A bio-electronic device according to claim 1 wherein said polyhydroxy oligomer is selected from the group of oligomers consisting of trehalose, maltose, cellobiose and zylotol.

5. A bio-electronic device according to claim 1 wherein said electronically active biochemical molecules are selected from the group consisting of electron donors and electron acceptors.

6. In a bio-electronic device wherein a layer of electronically active biochemical material is situated over the surface of a semiconductor layer and wherein the electronic activity of said biochemical material is reduced due to denaturization of said biochemical material upon binding to said surface, the improvement comprising:

reducing the denaturization of said electronically active biochemical material by providing a biochemical stabilization layer situated between said layer of electronically active biochemical material and the surface of said semiconductor layer, said biochemical stabilization layer consisting essentially of a polyhydroxy oligomer, said stabilization layer having an interior surface in contact with and bound to said semiconductor layer surface and an exterior surface onto which said electronically active biochemical material is bounded.

7. An improved bio-electronic device according to claim 6 wherein said semiconductor material is selected from the group consisting of silicon, indium tin oxide, tin dioxide and silicon tin oxide.

8. An improved bio-electronic device according to claim 6 wherein said semiconductor material is an amorphous material selected from the group consisting of gallium arsenide, indium phosphide, cadmium telluride and cadmium sulfide.

9. An improved bio-electronic device according to claim 6 wherein said polyhydroxy oligomer is selected from the group of oligomers consisting of trehalose, maltose, cellobiose and zylotol.

10. An improved bio-electronic device according to claim 6 wherein said electronically active biochemical molecule is selected from the group consisting of electron donors and electron acceptors.

* * * * *